United States Patent
Nebolsin

(10) Patent No.: US 12,077,551 B2
(45) Date of Patent: Sep. 3, 2024

(54) ZINC COMPLEX, PREPARATION THEREOF AND USE THEREOF FOR TRERAPY OF HUMAN AND ANIMAL DISEASES

(71) Applicant: OBSCHESTVO S OGRANICHENNOI OTVETSTVENNOSTIYU "Z THERAPEUTICS", Moscow (RU)

(72) Inventor: Vladimir Evgenievich Nebolsin, Borzye (RU)

(73) Assignee: OBSCHESTVO S OGRANICHENNOI OTVETSTVENNOSTIYU "Z THERAPEUTICS", Moscow (RU)

( * ) Notice: Subject to any disclaimer, the term of this patent is extended or adjusted under 35 U.S.C. 154(b) by 633 days.

(21) Appl. No.: 17/270,384

(22) PCT Filed: Aug. 22, 2019

(86) PCT No.: PCT/RU2019/050135
§ 371 (c)(1),
(2) Date: Feb. 22, 2021

(87) PCT Pub. No.: WO2020/040670
PCT Pub. Date: Feb. 27, 2020

(65) Prior Publication Data
US 2021/0246149 A1    Aug. 12, 2021

(30) Foreign Application Priority Data
Aug. 22, 2018 (RU) .......................... RU 2018130491

(51) Int. Cl.
*C07F 3/06* (2006.01)
*A61P 17/00* (2006.01)

(52) U.S. Cl.
CPC ................ *C07F 3/06* (2013.01); *A61P 17/00* (2018.01)

(58) Field of Classification Search
CPC .. C07F 3/06; A61P 17/00; A61P 37/00; A61K 31/417; A61K 33/30;
(Continued)

(56) References Cited

U.S. PATENT DOCUMENTS 5,582,817 A * 12/1996 Otsu .................... A61K 31/415
424/59

FOREIGN PATENT DOCUMENTS

RU     2180842 C2      3/2002
RU     2233152 C1 *    7/2004

OTHER PUBLICATIONS

Yamaguchi et al. Effect of zinc-chelating dipeptide on bone metabolism in weanling rats: comparison with beta-alanyl-L-histidinato zinc-related compounds. Peptides. 1994;15(4):671-3. (Year: 1994).*

(Continued)

*Primary Examiner* — Matthew P Coughlin
*Assistant Examiner* — Ashli Ariana Chicks
(74) *Attorney, Agent, or Firm* — BCF LLP

(57) ABSTRACT

The invention relates to a new zinc complex with gamma-L-glutamylhistamine with a metal/ligand ratio of 1/1. In particular, the invention relates to a compound of the formula (Continued)

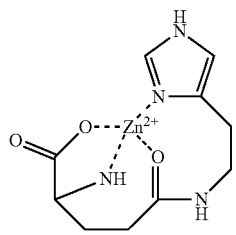

The complex according to the invention helps to restore the barrier functions of the epithelial tissue and suppresses the aberrant activity of the immune cells.

The invention also relates to the method of complex preparation and use of said zinc complex for the treatment of atopic dermatitis and other diseases associated with impaired barrier functions of epithelial tissue and the development of an aberrant inflammatory response.

The invention also relates to the use of the prepared complex for inhibiting glutaminyl cyclase.

This invention also concerns pharmaceutical compositions comprising a therapeutically effective amount of a compound of the invention.

14 Claims, 13 Drawing Sheets

(58) Field of Classification Search
CPC .............. A61K 31/4164; A61K 31/315; A61K 31/555; C07D 233/64
See application file for complete search history.

(56) References Cited

OTHER PUBLICATIONS

Katsoulidis et al. Guest-adaptable and water-stable peptide-based porous materials by imidazolate side chain control. Angewandte Chemie (International ed. in English) vol. 53,1 (2014): 193-8. (Year: 2014).*
Zhou et al. Interaction between Histidine and Zn(II) Metal Ions over a Wide pH as Revealed by Solid-State NMR Spectroscopy and DFT Calculations. The Journal of Physical Chemistry B 2013 117 (30), 8954-8965 (Year: 2013).*
Schilling et al. Glutaminyl cyclase inhibition attenuates pyroglutamate AB and Alzheimer's disease-like pathology. Nat Med 14, 1106-1111 (2008). (Year: 2008).*
Hartlage-Rübsamen et al. Isoglutaminyl cyclase contributes to CCL2-driven neuroinflammation in Alzheimer's disease. Acta Neuropathol. 2015;129(4):565-583. (Year: 2015).*
Van Etten et al. Aberrant cytokine signaling in leukemia. Oncogene. 2007;26(47):6738-6749. (Year: 2007).*
Luo et al. Cell, 2009, 136, pp. 823-837. (Year: 2009).*
The expanding family of interleukin-1 cytokines and their role in destructive inflammatory disorders. Clin Exp Immunol. 2007;149(2):217-225. (Year: 2007).*
Kalinin et al. Epithelial barrier function: assembly and structural features of the cornified cell envelope. BioEssays 24:789-800, 2002. (Year: 2002).*
Gaucher Disease, obtained from, https://my.clevelandclinic.org/health/diseases/16234-gaucher-disease Sep. 18, 2023. (Year: 2023).*
Alzheimer's disease, obtained from, https://www.nhs.uk/conditions/alzheimers-disease/prevention on Sep. 18, 2023. (Year: 2023).*
Rheumatoid Arthritis (RA), obtained from, https://www.cdc.gov/arthritis/basics/rheumatoid-arthritis.html Sep. 18, 2023. (Year: 2023).*
Abstract of Maarouf et al.,"Topical micronutrients in atopic dermatitis—An evidence-based review", Published on Jul. 17, 2018,e12659, https://doi.org/10.1111/dth.12659.
Schilling et al., "Identification of Human Glutaminyl Cyclase as a Metalloenzyme", Published in Dec. 2003, vol. 278, Issue 50, pp. 49773-49779, DOI:https://doi.org/10.1074/jbc.M309077200.
Revina et al., "Complexation between γ-L-glutamylhistamine, Zn(II) ions, and molecular oxygen in aqueous solutions of NaClO4 and Zn(NO3)2" Published in Feb. 2003, Russian Journal of Physical Chemistry 77(2):307-313.
Machine translation from Russian into English of Revina et al., "Complexation between γ-L-glutamylhistamine, Zn(II)ions, and molecular oxygen in aqueous solutions of NaClO4 and Zn(NO3)2" prepared online on Aug. 20, 2022.
International Search Report mailed on Dec. 5, 2019 in respect of PCT/RU2019/050135.
Office Action dated Feb. 24, 2022 issued in respect of the Eurasian patent application EA202190543.
Gupta, Mrinal : "Zinc Therapy in Dermatology: A Review", Dermatology Research and Practice, vol. 2014, Jan. 1, 2014 (Jan. 1, 2014), pp. 1-11.
Extended European Search Report mailed on Apr. 8, 2022 in respect of the related European Patent Application 19851160.2.

* cited by examiner

ZINC COMPLEX, PREPARATION THEREOF AND USE THEREOF FOR TRERAPY OF HUMAN AND ANIMAL DISEASES

CROSS REFERENCE TO RELATED APPLICATIONS

This application is a national stage application under 35 U.S.C. § 371 of International Application No. PCT/RU2019/050135, filed internationally on Aug. 22, 2019, which claims priority to Russian Application No. 2018130491, filed on Aug. 22, 2018, the contents of which is hereby incorporated by reference.

FIELD OF THE INVENTION

This invention relates to a novel zinc complex of gamma-L-glutamylhistamine, which restores barrier functions of epithelial tissue and suppresses the aberrant activity of immune cells. The present invention also relates to the preparation and use of the specified zinc complex for the treatment of atopic dermatitis and other diseases associated with impaired epithelial tissue barrier functions and the development of an aberrant inflammatory response.

BACKGROUND OF THE INVENTION

The epithelial barrier plays a critical role in human and animal organism. The epithelial barrier prevents a penetration of various substances, allergens, and bacteria into the internal environment of the body. Impairment of the barrier functions of epithelial tissue makes a significant contribution to the pathogenesis of several diseases, such as inflammatory diseases of the oral cavity (stomatitis, gingivitis, pharyngitis, etc.), diseases of the gastrointestinal tract (colitis, enteritis, intestinal autointoxication, irritable bowel syndrome, malabsorption syndrome, recurrent diarrhea, etc.), allergic diseases (allergic rhinitis, bronchial asthma, atopic dermatitis, etc.) [Recent Pat Antiinfect Drug Discov. 2015; 10 (2): 84-97; Current Pediatrics. 2013; 12 (2): 12-19; Bulletin of Siberian Medicine. 2017; 16 (2) 32-46]. Given the key role of the barrier functions of epithelial tissue in the development of inflammatory and allergic diseases, the strategy aimed at restoring the barrier functions of epithelial tissue is of primary importance for treatment for many pathological conditions in humans. In particular, topical therapy is of leading importance in the treatment of atopic dermatitis, that aims to restore damaged epithelium, improve the barrier functions of the skin, hydrate the skin, as well as to prevent and eliminate secondary infection [Pediatrics. 2014 December; 134 (6): e1735-44].

Zinc is one of the key trace elements that maintain the barrier functions of the skin, so its anti-inflammatory, antioxidant and antibacterial properties make it one of the most used trace elements in dermatology [FEMS Microbiol Lett. 2008 February; 279 (1): 71-76]. Zinc is an essential component of matrix metalloproteinases that control epithelial remodeling and is a key player in epithelial cell growth, wound healing and maintenance of skin barrier functions [Front Biosci (Landmark Ed). 2017 Mar. 1; 22: 1469-1492]. Recent studies have shown that the severity of symptoms of atopic dermatitis negatively correlates with the zinc concentration in the erythrocytes of patients [Postepy Dermatol Alergol. 2016 October; 33 (5): 349-352]. Moreover, the use of zinc compounds leads to a decrease in the severity of symptoms of atopic dermatitis in preclinical and clinical studies [Biol Trace Elem Res. 2017 September; 179 (1): 110-116; Clin Cosmet Investig Dermatol. 2013 May 6; 6: 115-21; Acta Derm Venereol. 2014 September; 94 (5): 558-62]. It has been shown on animal models of atopic dermatitis that the use of zinc compounds restores the thickness of epithelial tissues and reduces the severity of local inflammation of the skin [Dermatol Ther. 2018 Jul. 17: e12659].

It should be noted that impairment of the barrier functions of epithelial tissue in many cases is associated with the development of an aberrant inflammatory response, which, in turn, induces further cell destruction and degradation of the barrier functions of the epithelium. For example, in patients with atopic dermatitis, impairment of the barrier functions of the skin leads to its colonization by opportunistic bacteria, including *S. aureus* [Br J Dermatol. 1998 December; 139 Suppl 53: 13-6]. Bacterial contamination of the skin with opportunistic microorganisms leads to the development of an excessive inflammatory reaction and aberrant chemotaxis of the immune cells (mainly lymphocytes, eosinophils, dendritic and mast cells) that produce pro-inflammatory cytokines. Pro-inflammatory cytokines and reactive oxygen species secreted by the immune cells induce further degradation of skin barrier functions which serves as self-sustaining positive feedback thus ensuring the progression of the disease into the chronic phase [J. Clin. Diagn. Res. 2013 December; 7 (12): 2683-2685]. Thus, the suppression of the aberrant activity of the immune cells by inhibiting chemotaxis thereof may be the key point in the treatment of atopic dermatitis, as well as other diseases of humans and animals.

Chemokines of the CCL family (CCL2, CCL7, CCL8, CCL13) are potent factors in the chemotaxis of monocytes, macrophages, eosinophils, T-lymphocytes and dendritic cells in mammals [Biochem. J. 2012 Mar. 1; 442 (2): 403-12; Postepy Dermatol. Alergol. 2014 May; 31 (2): 84-91]. Members of the CCL family (CCL2, CCL7, CCL8, CCL13), fractalkine, as well as a number of other hormones and secretory proteins, contain the pyroglutamic acid (pE) residue, whose role is to protect against degradation thereof by aminopeptidases [Chem Immunol. 1999; 72: 42-56; Biochemistry. 1999 Oct. 5; 38 (40): 13013-25]1. Pyroglutamination of the N-terminal residue is catalyzed by the enzyme glutaminyl cyclase (QPCT or QC) [J Biol Chem. 2003 Dec. 12; 278 (50): 49773-9; J Mol Biol. 2008 Jun. 20; 379 (5): 966-80]. In the course of experimental studies, it has been shown that glutaminyl cyclase inhibition leads to a sharp decrease in the chemoattractant activity of non-pyroglutaminated forms of chemokines CCL2, CCL7, CCL8 and CCL13 [Biochem. J. (2012) 442, 403-412) and fractalkine (Biosci Rep. 2017 Aug. 23; 37 (4)]. Thus, pyroglutamination of chemokines of the CCL family is a necessary step in CCL-mediated chemotaxis of immune cells, so the strategy aimed to inhibition of glutaminyl cyclase may represent a possible strategy to modulate an aberrant inflammatory response and reduce the activity of immune cells.

To date, zinc complexes of glutaminyl cyclase inhibitors, as well as their preparation and therapeutic use, have not been described. At the same time, glutaminyl cyclase inhibitors are known, including sulfolipids [WO 2017/046256, publ. Mar. 23, 2017, HOCHSCHULE ANHALT, DE], flavonoid derivatives [Bioorg Med Chem. 2016 May 15; 24 (10): 2280-6], pyridine derivatives [US 2015/0291632, publ. 15 Oct. 2015, Dow AgroSciences LLC, US] and some small molecules described recently [J. Med. Chem. 2017 Mar. 23; 60 (6): 2573-2590; WO 2014/193974, US 2015/0291557]. Also, glutaminyl cyclase inhibitors are described in the publications of Probiodrug Aktiengesellschaft company [J.

Biol. Chem. 2003 Dec. 12; 278 (50): 49773-9]. These articles describe glutaminyl cyclase inhibitors based on imidazole derivatives. However, the publications of Probiodrug Aktiengesellschaft do not include zinc complexes of glutaminyl cyclase inhibitors to begin with, and the structures of the compounds published by the company Probiodrug Aktiengesellschaft include imidazole that contains an aliphatic substituent located at one of the nitrogen atoms. The introduction of an aliphatic substituent decreases the metabolic stability of the compounds. In addition, the presence of an aliphatic substituent increases the hydrophobicity of the compounds and increases the systemic bioavailability of the compounds, which is apparently unnecessary for the treatment of atopic dermatitis and other diseases associated with impaired barrier functions of epithelial tissue.

To dateit is not known any drug based on the zinc complex of a glutaminyl cyclase inhibitor that could be used for the treatment of atopic dermatitis or other diseases associated with impaired barrier functions of epithelial tissue and/or aberrant activity of immune cells, therefore, an unmet need for the development and therapeutic use of novel effective drugs based on zinc complexes of glutaminyl cyclase inhibitors still remains.

The purpose of the present invention is to develop a new effective chemical compound that is effective in restoring the barrier functions of epithelial tissue and capable of inhibiting glutaminyl cyclase enzyme in treating atopic dermatitis or other diseases associated with impaired barrier functions of the epithelium and aberrant activity of immune cells.

BRIEF SUMMARY OF THE INVENTION

The purpose of the present invention is to develop a novel drug that is effective for the treatment of diseases associated with impaired barrier functions of epithelial tissue and aberrant activity of immune cells, atopic dermatitis in particular, as well as other diseases.

The technical result of this invention is to provide a novel chemical compound effective for the treatment of atopic dermatitis, as well as other diseases associated with impaired barrier functions of epithelial tissue and/or aberrant activity of immune cells.

The specified technical result is achieved by providing a compound of the zinc complex of gamma-L-glutamylhistamine (metal: ligand ratio=1:1).

Based on the studies carried out, which are described in detail in this description, the Applicant suggests that the structure of the resulting complex can be described by the following structural formula:

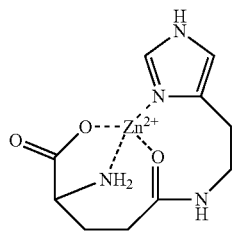

The specified zinc complex (Compound 1) or hydrate, solvate, or pharmaceutically acceptable salt thereof, is effective for the treatment of atopic dermatitis, as well as other diseases associated with impaired barrier functions of epithelial tissue and aberrant activity of immune cells.

Another technical result of the present invention is the use of the prepared zinc complex of gamma-L-glutamylhistamine (Compound 1) or hydrate/solvate thereof for preventing and/or treating atopic dermatitis, as well as other diseases associated with impaired barrier functions of epithelial tissue and aberrant activity of the immune cells.

Another technical result of the present invention is a use of a novel zinc complex of gamma-L-glutamylhistamine or a hydrate, solvate, or a pharmaceutically acceptable salt thereof for preparation of a pharmaceutical composition for preventing and/or treating a disorder associated with aberrant activity of immune cells, in particular with aberrant chemotaxis of immune cells.

In addition, the invention provides pharmaceutical compositions for preventing and/or treating atopic dermatitis, as well as other diseases associated with impaired barrier functions of epithelial tissue and aberrant activity of immune cells which contain an effective amount of a compound of the invention and at least one pharmaceutically acceptable agent/excipient. In some embodiments, the agent is a pharmaceutically acceptable carrier and/or excipient.

The invention also includes a method for preventing and/or treating atopic dermatitis, as well as other disorders associated with impaired barrier functions of epithelial tissue and aberrant activity of immune cells in an organism, the method comprising administering a pharmaceutical composition according to the invention to a subject. In particular cases of the invention embodiment, the subject is a human or an animal.

Zinc complexes of gamma-L-glutamylhistamine have not been described in the prior art, however, a pseudopeptide of gamma-L-glutamylhistamine is known, first isolated in trace amounts from rat and mollusc nervous tissues [J. Neurochem. -1976. -vol. 27.-pp. 1461-1463; J. Neurochemistry. -1977. -vol. 29. -pp. 633-638.]. The production of gamma-L-glutamylhistamine is described in patent RU2141968, publ. Nov. 27, 1999. The use of a cream based on gamma-L-glutamylhistamine is described in patent RU 2233152, publ. Jul. 27, 2004.

DETAILED DESCRIPTION OF THE INVENTION

Figure 1:
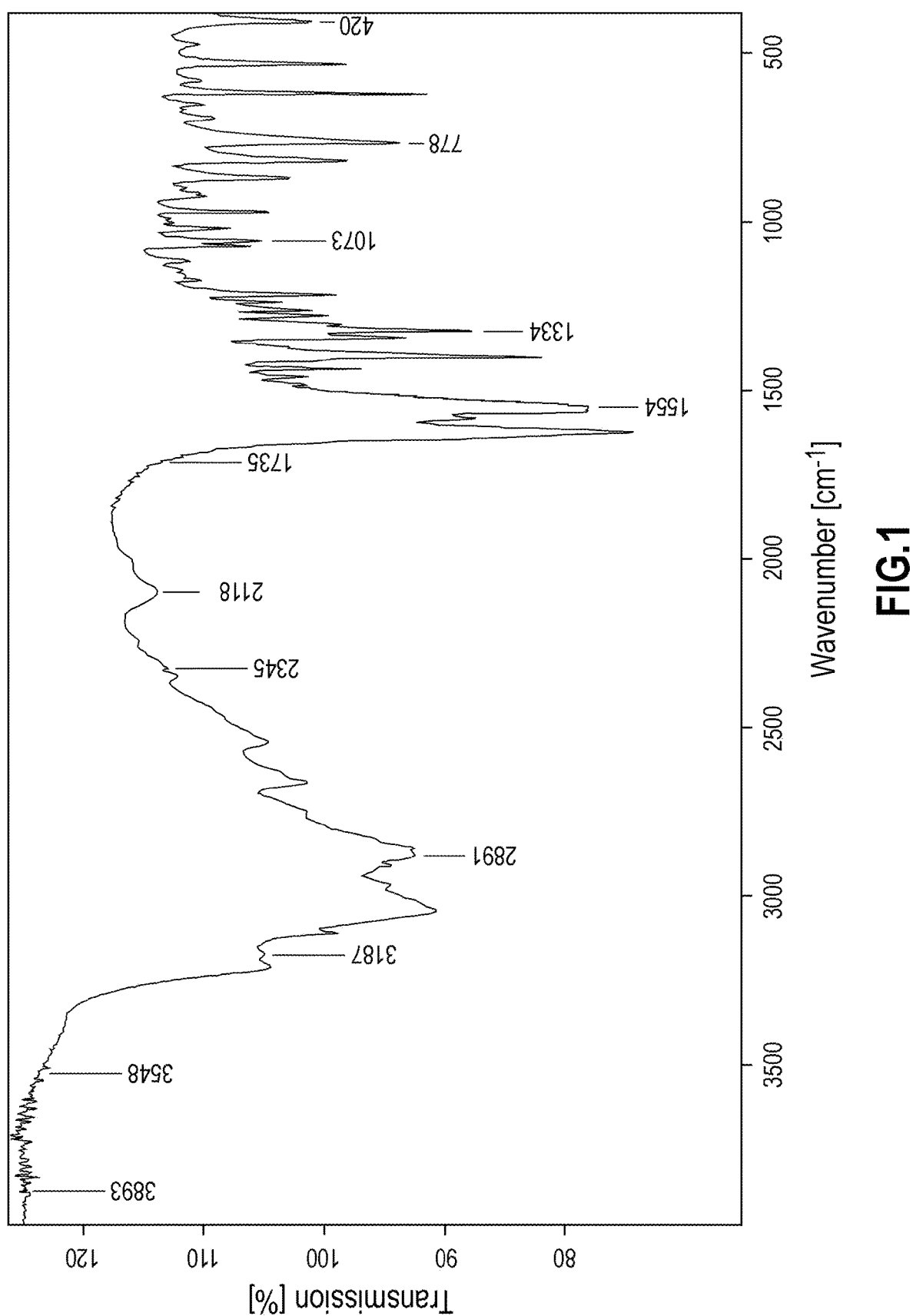
FIG. 1. IR spectrum of a gamma-L-glutamylhistamine pseudopeptide (ligand) sample.

As indicated above, while no zinc complex of gamma-L-glutamylhistamine was described in the prior art, the pseudopeptide gamma-L-glutamylhistamine is known as a substance being first isolated from rat and mollusc nervous tissues in trace amounts [J. Neurochem. -1976. -vol. 27.-pp. 1461-1463; J. Neurochemistry. -1977. -vol. 29. -pp. 633-638]. The preparation of gamma-L-glutamylhistamine is also disclosed in the patent RU 2141968. These works describe gamma-L-glutamylhistamine, which is a pseudopeptide with antioxidant, antiradical, lipid-regulating, hypoglycemic, anti-asthmatic, antiviral, antibacterial, anti-tumor, anti-inflammatory, antimetastatic, adaptogenic action, which is able to modulate the metabolism of arachidonic acid, prevent the manifestations of diabetes mellitus, obesity, coronary artery disease, stress conditions, hepatitis, cirrhosis, toxic liver damage, alcoholism, radiation damage, and gerontological changes.

At the same time, these works do not provide any data on zinc complexes of gamma-L-glutamylhistamine, methods of preparation thereof or research data of their biological activity. At the same time, it should be noted that the zinc complex of gamma-L-glutamylhistamine cannot be obtained by simple mixing of zinc salts and gamma-L-glutamylhistamine, since under these conditions a mixture of zinc salts and free gamma-L-glutamylhistamine is formed.

Working on the present invention, the author/applicant has developed a method for producing a stable zinc complex of gamma-L-glutamylhistamine having a metal/ligand ratio of 1/1.

Compound 1

In the process of research focused on the specific pharmacological activity of gamma-L-glutamylhistamine zinc complex (Compound 1) prepared by the applicant, in a model of atopic dermatitis, it was shown that Compound 1 demonstrates a significantly higher therapeutic activity in comparison with the free ligand of gamma-L-glutamylhistamine. The administration of Compound I (0.01% wt cream) to the skin reduces the influx of inflammatory cells (monocytes, dendritic cells, eosinophils and neutrophils) into the epidermis and dermis of the skin to the level of intact animals, as well as reduces other microscopic manifestations of atopic dermatitis. Thus, Compound 1 has been shown to affect the chemotaxis of immune cells. Reducing the influx of immune cells can be used in the treatment of a number of diseases associated with aberrant activity of immune cells.

Research studies conducted by the applicant have shown that the observed therapeutic effect of Compound 1 is related to the ability of this compound to inhibit the activity of glutaminyl cyclase.

Thus, Compound 1 (zinc complex of gamma-L-glutamylhistamine having a metal/ligand ratio 1/1) is a novel chemical compound useful for the treatment of atopic dermatitis and other diseases associated with impaired epithelial tissue barrier functions and aberrant activity of immune cells.

Terms and Definitions

The term "Compound I" refers to the zinc complex of gamma-L-glutamylhistamine having a metal:ligand ratio of 1:1.

Specifically, this complex can be represented by the structural formula:

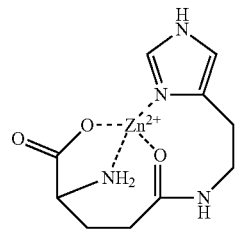

or a pharmaceutically acceptable salt thereof.

The term "C" when used with reference to temperature means a centigrade or Celsius temperature scale.

The term "$IC_{50}$" represents the test compound concentration which results in half-maximal inhibition of the enzyme.

The term "solvate" is used to describe a molecular complex containing a compound of the invention and one or more molecules of a pharmaceutically acceptable solvent, for example, ethanol. The term "hydrate" is used when the specified solvent is water.

The term "aberrant activity" of immune cells in this document refers to an activity which is significantly different from the baseline level of immune cells activity in the subject in the absence of pathology. Aberrant activity can be caused by an excessive influx of immune cells to an organ or tissue, disruption of processes leading to the activation of immune cells, deregulation of processes associated with the immune cells death, as well as other factors.

The term "excipient" means any pharmaceutically acceptable substance of inorganic or organic origin, included in the composition of a medicinal product or used in the manufacturing process, preparation of a medicinal product to impart the necessary physicochemical properties.

The term "glutaminyl cyclase" refers to an aminoacyltransferase enzyme involved in the conversion of N-terminal glutamine to pyroglutamine in various peptide substrates. The formation of N-terminal pyroglutamate protects biologically active peptides, hormones, and chemokines (for example, thyrotropin-releasing hormone, β-chemokine ligand-2) from degradation by exopeptidases and can increase the affinity of ligands for their receptors in some cases.

The term "chemotaxis" refers to the directed movement of cells in response to a chemical stimulus. Chemotaxis is based on the ability of a cell to respond to a concentration gradient of a chemotactic mediator. Chemotaxis is the process by which immune cells leave the vascular bed and migrate to damaged tissue. The leading role in chemotaxis is played by chemotactic substances, or chemoattractants. CCL2 chemokine is one of the most potent chemoattractants for monocytes and macrophages.

The terms "treatment", "therapy" "treating" encompass the treating pathological conditions in mammals, preferably in humans, and include: a) ameliorating, b) breaking (terminating) the course of the disease, c) alleviating the severity of the disease, i. e. initiation of regression of the disease, d) reversal of the disease or condition to which the term applies, or one or more symptoms of the disease or condition.

The term "prophylaxis", or "prevention" encompasses the elimination of risk factors, as well as prophylactic treatment of subclinical stages of the disease in mammals, preferably in humans, aimed at reducing the likelihood of the occurrence of clinical stages of the disease. Subjects for prophylactic therapy are selected on the basis of factors that are known to be associated with an increased risk of clinical disease compared with the general population. Preventive therapy includes a) primary prevention and b) secondary prevention. Primary prevention refers to prophylactic treatment/preventive measures for patients who have not yet reached the clinical stage of the disease. Secondary prevention is the prevention of recurrence of the same or similar clinical condition of the disease.

Compound I, which is the subject of this invention, shows promise for treating diseases associated with impaired barrier functions of epithelial tissue and aberrant activity of immune cells, and, in particular, for treating diseases associated with aberrant chemotaxis of immune cells, preferably for the therapy of atopic dermatitis. In some particular embodiments, a compound of the invention may be used for the treatment of other diseases caused by impaired barrier functions of epithelial tissue and aberrant activity of immune cells.

A Method for Therapeutic Use of the Compound

The subject of this invention also includes administering a therapeutically effective amount of a compound of this invention to a subject in need of appropriate treatment. Therapeutically effective amount is the amount of a compound administered or delivered to a patient in such a way that the patient is most likely to exhibit the desired response to treatment (prophylaxis). The exact amount required may vary from subject to subject, depending on the age, body weight and general condition of the subject, the severity of the disease, the method of drug administration, whether it is used in combination with other drugs, and the like.

The compound of the invention or a pharmaceutical composition comprising the compound can be administered to a subject in need in any amount and by any route of administration effective for treating or preventing a disease (topical route of administration is preferred).

Following mixing the compound with a specific suitable pharmaceutically acceptable carrier at the desired dosage, the compositions of the invention can be administered topically to humans or other animals and the like.

The administering can be carried out both once or several times per day, per week (or by any other time interval), or occasionally as needed. In addition, the compound can be administered to a subject daily for a specified number of days (for example, 2-10 days), followed by an interval during which the medication is not administered (for example, 1-30 days).

In case a compound of the invention is used as part of a combination therapy regimen, the dose of each of the combination therapy components is administered over the desired treatment period. The active ingredients that make up the combination therapy can be administered to the subject either as a lump sum, in the form of a dosage containing all the components, or in the form of individual dosages of the components.

Pharmaceutical Compositions

The invention also relates to pharmaceutical compositions that contain a compound of the invention (or a prodrug or other pharmaceutically acceptable derivative) and one or more pharmaceutically acceptable carriers, adjuvants, diluents and/or excipients, such as those that can be co-administered to a subject in combination with the compound of the present invention, under condition that they do not affect the pharmacological activity of this compound and are non-toxic when administered in doses sufficient to deliver a therapeutic amount of the compound.

The invention also relates to a method for producing a zinc complex with gamma-L-glutamylhistamine, the method comprising stirring a mixture of zinc acetate and gamma-L-glutamylhistamine in a polar solvent, preferably in a polar solvent, isolating the product precipitate and drying the resulting product, which represents a zinc complex of gamma-L D-glutamylhistamine having a metal/ligand ratio of 1/1. Preferred solvents are methanol or water, or combinations thereof. The process preferably uses aqueous zinc acetate, zinc acetate dihydrate in particular. Stirring of the mixture is carried out at the temperature range of 15 to 50 degrees Celsius, preferably 15 to 40 degrees Celsius if methanol is used as a solvent or at the temperature of 15 to 90 degrees Celsius if water is used as a solvent.

The compound of the invention can be used in a form of a pharmaceutically acceptable salt thereof. Specifically, organic and inorganic acid addition salts well known to the person skilled in the art, for example, hydrochloride or acetate, can be prepared.

Pharmaceutical compositions according to the invention comprise a compound of this invention along with pharmaceutically acceptable carriers, which may include any solvents, diluents, dispersions or suspensions known to those skilled in the art, surfactants, isotonic agents, thickeners and emulsifiers, preservatives, binders, lubricants, etc., suitable for a particular dosage form. Suitable materials that can serve as pharmaceutically acceptable carriers include, mono- and oligosaccharides, and derivatives thereof; gelatin; talc; excipients such as cocoa butter and suppository wax; oils such as peanut, cottonseed, safrole, sesame, olive, corn, and soybean oils; glycols such as propylene glycol; esters such as ethyl oleate and ethyl laurate; agar; buffering agents such as magnesium hydroxide and aluminum hydroxide; alginic acid; pyrogen-free water; isotonic solution, Ringer's solution; ethyl alcohol and phosphate buffers. Also, the composition may include other non-toxic compatible lubricants such as sodium lauryl sulfate and magnesium stearate, as well as colorants, film-formers, sweeteners, flavorings and aromas, preservatives and antioxidants.

The subject of this invention also covers dosage forms, a class of pharmaceutical compositions, the composition of which is optimized for a specific route of administering to a subject in need thereof in a therapeutically effective dose, for example, for local administering to a subject.

The dosage forms of the present invention may contain formulations prepared by liposome methods, microencapsulation methods, nanoform preparation methods, or other methods known in the art.

For topical administration, forms known to those skilled in the art can be used, such as ointments, creams and suspensions, which contain pharmacologically compatible agents, for example, propylene glycol or butylene glycol.

Examples of Pharmaceutical Compositions

The compound described in this invention can be used for preventing and/or treating diseases in humans or animals in the form of the following compositions:

Ointment, ml
Active ingredient 40 mg
Ethanol 300 µl
Water 300 µl
1-dodecylazacycloheptanone 50 µl
Propylene glycol up to 1 ml
Cream I wt. %
Active ingredient 0.005-0.5
Oil component 10.0-15.0
Cosmetic stearin 2.0-3.0
Emulsifier 1.0-3.0

Emulsion wax 1.0-3.0
Triethanolamine 0.1-0.6
Vitamin A 0.003-0.05
Distilled glycerin 2.0-3.0
Antioxidant 0.05-0.075
Preservative 0.15-0.25
Tea tree oil 0.3-0.5
Purified drinking water up to 100t
Cream II wt. %
Active ingredient 0.01
Vegetable oil 15.0
Cosmetic stearin 0.75
Emulsifier PG-3 2.25
Emulsion wax 2.25
Triethanolamine 0.1
Vitamin A 0.028
Sorbitol 2.0-3.0
Vitamin E 1.5
Monomuls® 90-0 18 0.75
Nipazole 0.2
Nipagin 0.3
Tea tree oil 0.3-0.5
Purified drinking water up to 100t
Cream III wt. %
Active ingredient 0.1
Vegetable oil 15.0
Cosmetic stearin 0.75
Emulsifier PG-3 2.25
Emulsion wax 2.25
Triethanolamine 0.1
Vitamin A 0.028
Sorbitol 2.0-3.0
Vitamin E 1.5
Monomuls® 90-0 18 0.75
Nipazole 0.2
Nipagin 0.3
Tea tree oil 0.3-0.5
Purified drinking water up to 100%
Cream IV wt. %
Active ingredient 0.3
Vegetable oil 15.0
Cosmetic stearin 0.75
Emulsifier PG-3 2.25
Emulsion wax 2.25
Triethanolamine 0.1
Vitamin A 0.028
Sorbitol 2.0-3.0
Vitamin E 1.5
Monomuls® 90-O 18 0.75
Nipazole 0.2
Nipagin 0.3
Tea tree oil 0.3-0.5
Purified drinking water up to 100%

In case of an ointment, the preferred oil component is vegetable oil, mineral oil, or a mixture thereof. The vegetable oil can be olive oil, sunflower oil, or a mixture of both. The mineral oil can be liquid petroleum jelly. Polyesters of unsaturated fatty acids in glycerol (emulsifier PG-3) can be used as an emulsifier. Vitamin A may be present as retinol palmitate. The preferred antioxidant is tocopherol acetate, and the preservative is at least one lower alkyl ester of paraoxybenzoic acid, for example, methyl or propyl esters.

These formulations can be prepared in accordance with standard pharmaceutical procedures.

Use of Compound I in Combination Therapy While Compound I of this invention can be administered as an standalone active ingredient, it can also be used in combination with one or more other agents, wherein in particular, the other agent can be represented by an antibiotic, NSAID (non-steroidal anti-inflammatory agent) or other anti-inflammatory agent, glucocorticosteroid, calcineurin inhibitor, antihistamine, membrane stabilizing agent, immunotropic agent, etc. When administered together, the therapeutic agents can be in different dosage forms that are administered simultaneously or sequentially at different times, or the therapeutic agents can be combined into a single dosage form.

The phrase "combination therapy" in relation to a compound of this invention in combination with other pharmaceutical agents means the simultaneous or sequential administration of all agents that provide the beneficial effects of the drug combination. Co-administration means, in particular, co-delivery of the agents, for example, in one ointment, cream, tablet, capsule, injection or other form, with a fixed ratio of active substances, as well as simultaneous delivery of each compound in several separate dosage forms, respectively.

Thus, the administering of a compound of this invention can be carried out in combination with additional therapies known to those skilled in the field of the preventive medicine and treating related diseases, including the use of antibacterial, cytostatic and cytotoxic drugs, drugs to suppress symptoms or side effects of one of the drugs.

If the formulation is represented by a dosage form, such a combination should comprise compound of this invention in an acceptable dose range. Compound I of this invention can also be administered to a patient sequentially with other agents, when combining of these drugs is not possible. The invention is not limited to the sequence order of administering; the compound of this invention can be co-administered to a subject before or after administering of another medication.

EXAMPLES OF THE INVENTION EMBODIMENTS

Elemental Analysis of Samples

Elemental composition studies of the samples were carried out using a multi EA 5000 Elemental Analyzer, Analytik Jena. For the analysis, a weighed portion of a sample about 20 mg (accurately weighed) was placed in an autosampler cell. After filling the device with an inert gas (helium), 10 cm$^3$ of oxygen purified from nitrogen, carbon, and moisture were added and the study sample was burned at a temperature of ~1000° C. To remove excess oxygen, combustion products were passed over metallic copper at the temperature of 750° C. Then a mixture of gases ($CO_2$, $N_2$, and $H_2O$) was passed through an adsorption trap to collect moisture and determine the amount of hydrogen. Then a mixture of nitrogen and carbon monoxide was fed into a gas chromatographic column and separated into components, which were transferred by a carrier gas to a chemiluminescence detector CLD (to analyze the nitrogen content in the gas mixture) and an NDIR infrared detector (to analyze the content of carbon monoxide in the gas mixture). The calculation of the content of each of the determined elements in the test sample was carried out using the software package multiWin.

IR spectra were recorded on an IFS-113v Bruker IR spectrometer in the range 4000 . . . 400 cm$^{-1}$ with a resolution of 1 cm$^{-1}$. To prepare the samples, the zinc complex of gamma-L-glutamylhistamine was triturated with KBr (5 mg of substance per 100 mg of KBr), pressed into tablets, and used to evaluate the spectrum.

Example 1 (not Included in the Invention). Mixing Zinc Chloride with Gamma-L-Glutamylhistamine This example demonstrates that the zinc complex of gamma-L-glutamylhistamine could not be prepared by simple mixing of the ingredients such as the zinc salts and gamma-L-glutamylhistamine, due to the formation of a mixture of zinc salts and free gamma-L-glutamylhistamine under these conditions.

For example, mixing zinc chloride aqueous solution with gamma-L-glutamylhistamine in a ratio of 1:2 and adding aqueous ammonia (until the medium is slightly alkaline) followed by the product precipitation results in the formation of a white crystalline substance. The elemental analysis data (see Table 1) show data values close to the calculated values for the complex compound, however the data cannot be regarded as evidence of the complex formation. The underestimated content of carbon and nitrogen in the samples indicates the probable formation of zinc hydroxide, which partially loses water during the analysis, may lead to underestimate values of other elements. The repeated elemental analysis of the complexes after additional coldwater wash leads to an even greater overestimation of the amount of hydrogen in the samples.

TABLE 1

Elemental analysis data for a sample isolated from the reaction of zinc chloride with gamma-L-glutamylhistamine

|  | C | H | N |
|---|---|---|---|
| Found (before water treatment) | 40.12 | 5.81 | 18.61 |
| Found (after water treatment) | 39.62 | 5.99 | 18.03 |
| Calculated | 44.17 | 5.56 | 20.60 |

Figure 2:
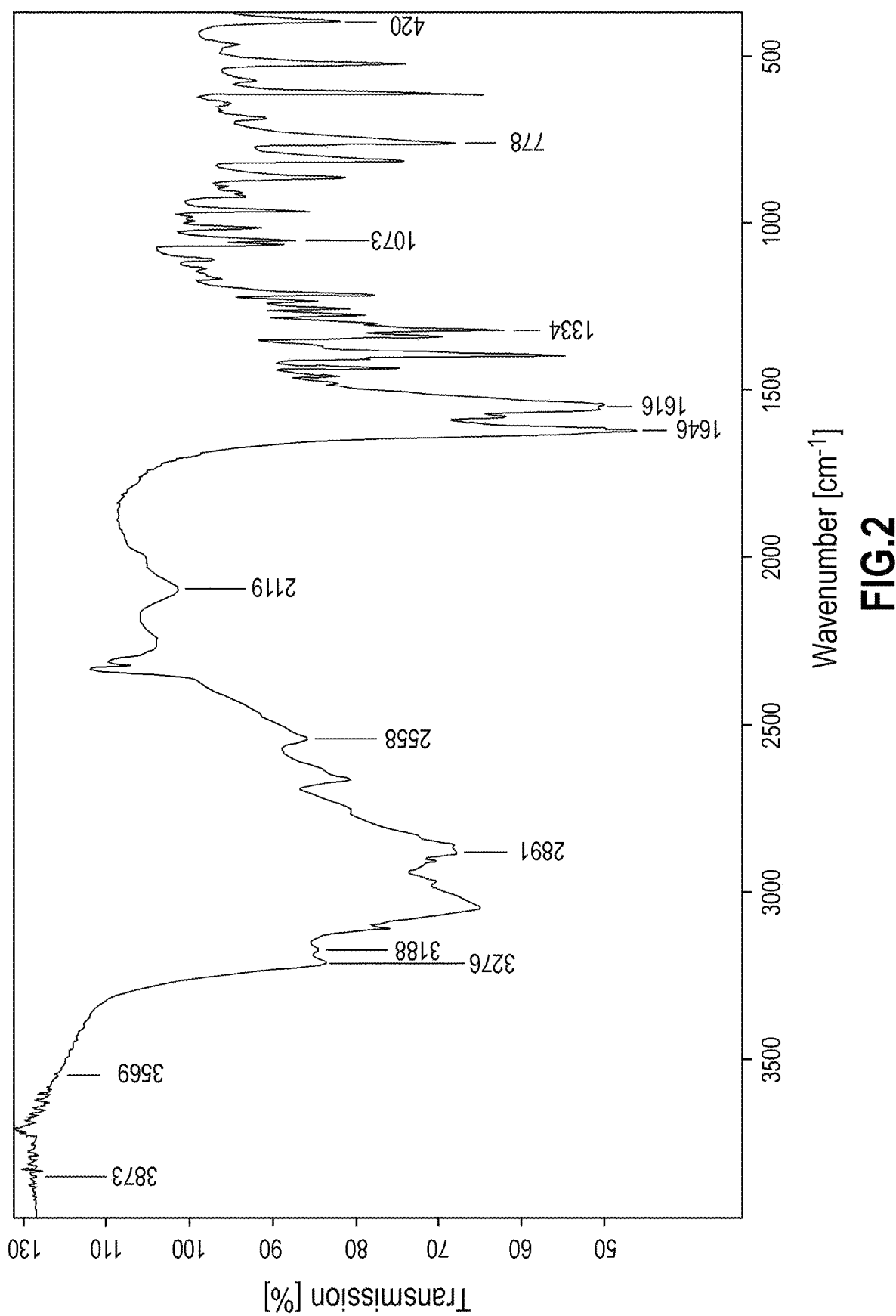
FIG. 2. IR spectrum of a product sample prepared by mixing a solution of zinc chloride and gamma-L-glutamylhistamine according to Example 1.

Furthermore, according to the data of IR spectroscopy, the IR spectra of the original gamma-L-glutamylhistamine and the product of mixing coincide (see FIGS. 1 and 2). The absence of shifts and the coincidence of the relative intensities of the absorption bands of C=O, —OH and —NH groups indicates that mixing zinc chloride with gamma-L-glutamylhistamine in Example 1, the original gamma-L-glutamylhistamine was isolated, and zinc is released in the form of an inorganic compound.

Example 2. Preparing a Zinc Complex According to the Invention (Method No. 1)

In the further study, the author has developed a method for obtaining a zinc complex with gamma-L-glutamylhistamine, which included the use of aqueous zinc acetate. 2.20 g (0.01 mol) $Zn(CH_3COO)_2*2H_2O$ was dissolved in 20 ml of methanol and added drop-by-drop, with vigorous stirring, to a solution of 2.40 g (0.01 mol) of gamma-L-glutamylhistamine and 1.08 g (0.02 mol) of freshly prepared sodium methoxide in 50 ml of methanol at room temperature. After approximately half the volume of the zinc acetate solution was added, a formation of white precipitate was observed. After adding all the zinc acetate solution, stirring was continued for about 4 hours, the product is filtered off, washed with water (4×10 ml) and is dried in a vacuum at 65° C. until its weight remains constant. Yield 2.67 g (88i).

2 test runs of this technique of the method embodiment were performed and a sample for elemental analysis was obtained from each run. According to the analysis of the elemental analysis data of these two samples resulting of the implementation of the method, a zinc complex with gamma-L-glutamylhistamine with a molar ratio of gamma-L-glutamylhistamine/zinc is formed—1/1 (see Table 2)

TABLE 2

Data of the elemental analysis of the sample isolated from the reaction mixture of zinc acetate with gamma-L-glutamylhistamine

|  | C | H | N |
|---|---|---|---|
| Found 1 | 39.17 | 4.73 | 18.02 |
| Found 2 | 37.26 | 4.80 | 18.110 |
| Calculated | 39.56 | 4.65 | 18.45 |

Follow-up complexometric titration of zinc was performed to confirm the complex composition and the obtained metal/ligand ratio. To determine the zinc content, the product was mineralized as follows: a sample of the product weighing ~70 mg was heated with a fivefold amount of concentrated sulfuric acid until the sample was completely charred. Then, ~1.5 ml of 30 vol % hydrogen peroxide was added to the residue and boiled for ~10 minutes. The residue was transferred into a 25 ml conical flask, and ~10 ml of an ammonia buffer mixture (pH=10) and a small amount of dry indicator of eriochrome black T were added.

The contents of the flask were thoroughly mixed until the indicator was completely dissolved and the solution became raspberry-colored. The sample was titrated with 0.02 M EDTA solution until the crimson color changed through violet to bright blue. Finally, it was shown that the content of zinc in the prepared product is 21.5%, which is consistent with the theoretically calculated value (21.1%) corresponding to a zinc complex having a metal: ligand ratio of 1:1.

Figure 3:
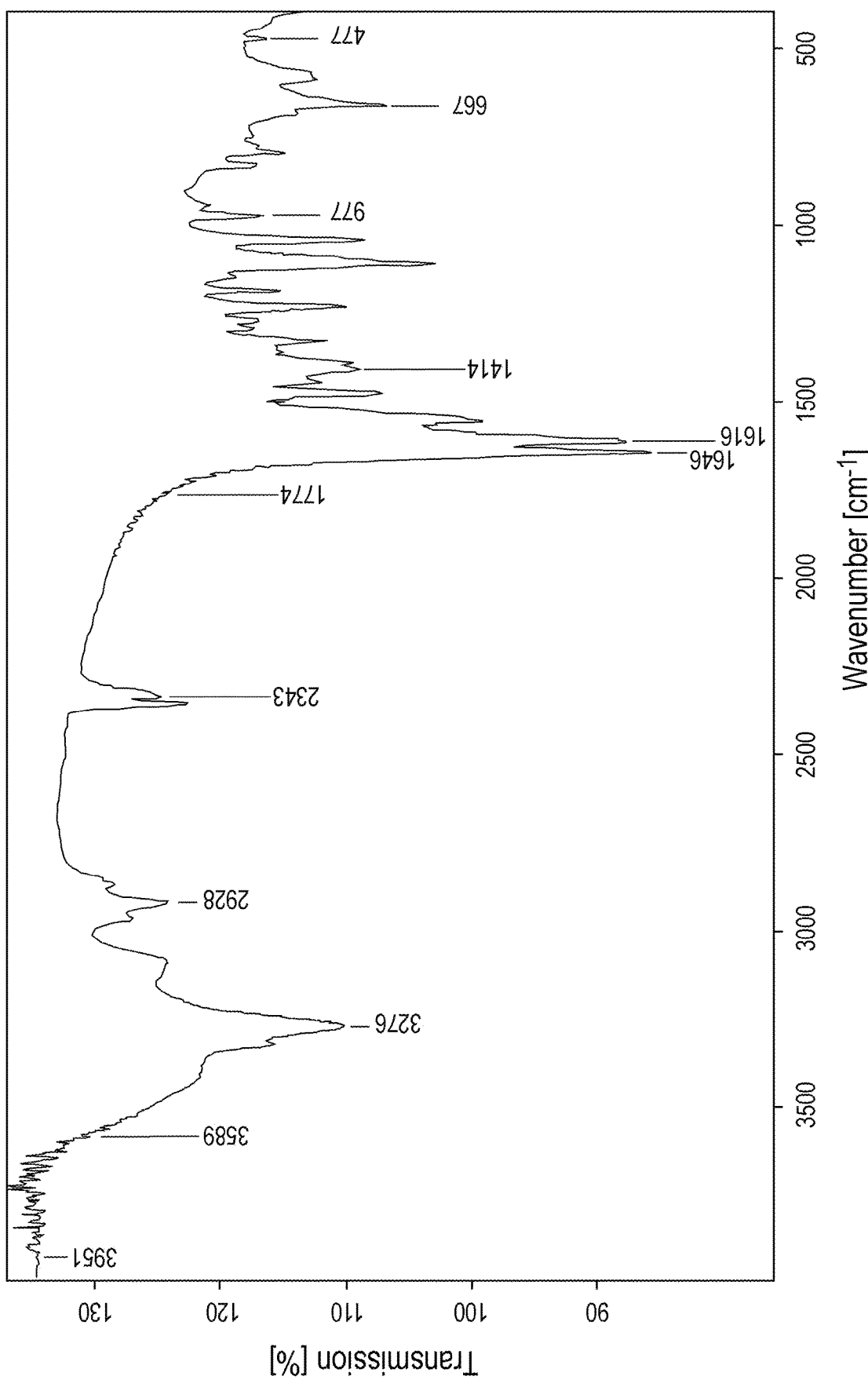
FIG. 3. IR spectrum of a sample of the zinc complex of gamma-L-glutamylhistamine according to example 2.

In the IR spectrum of the product (see FIG. 3), two strong bands of the carbonyl group are observed: 1616 $cm^{-1}$ and 1646 $cm^{-1}$. At the same time, the structure and frequencies of absorption differ significantly from those in the spectrum of free gamma-L-glutamylhistamine (see FIG. 1): the band of the carboxyl group is shifted towards higher frequencies due to coordination with zinc. Also, in the IR spectrum of the product there is an intense absorption band at 3276 $cm^{-1}$, which is absent in the spectrum of gamma-L-glutamylhistamine. It can be attributed to the vibrations of the N—H bond in the amide fragment, or the N—H bond of the imidazole system. In addition, in the IR spectra of the product, compared to the spectrum of gamma-L-glutamylhistamine, there are multiple changes in the areas of fingerprints and vibrations of CH bonds, indicating the absence of free gamma-L-glutamylhistamine in the sample.

The prepared resulting product is insoluble in solvents which are used to record NMR spectra.

Figure 6:
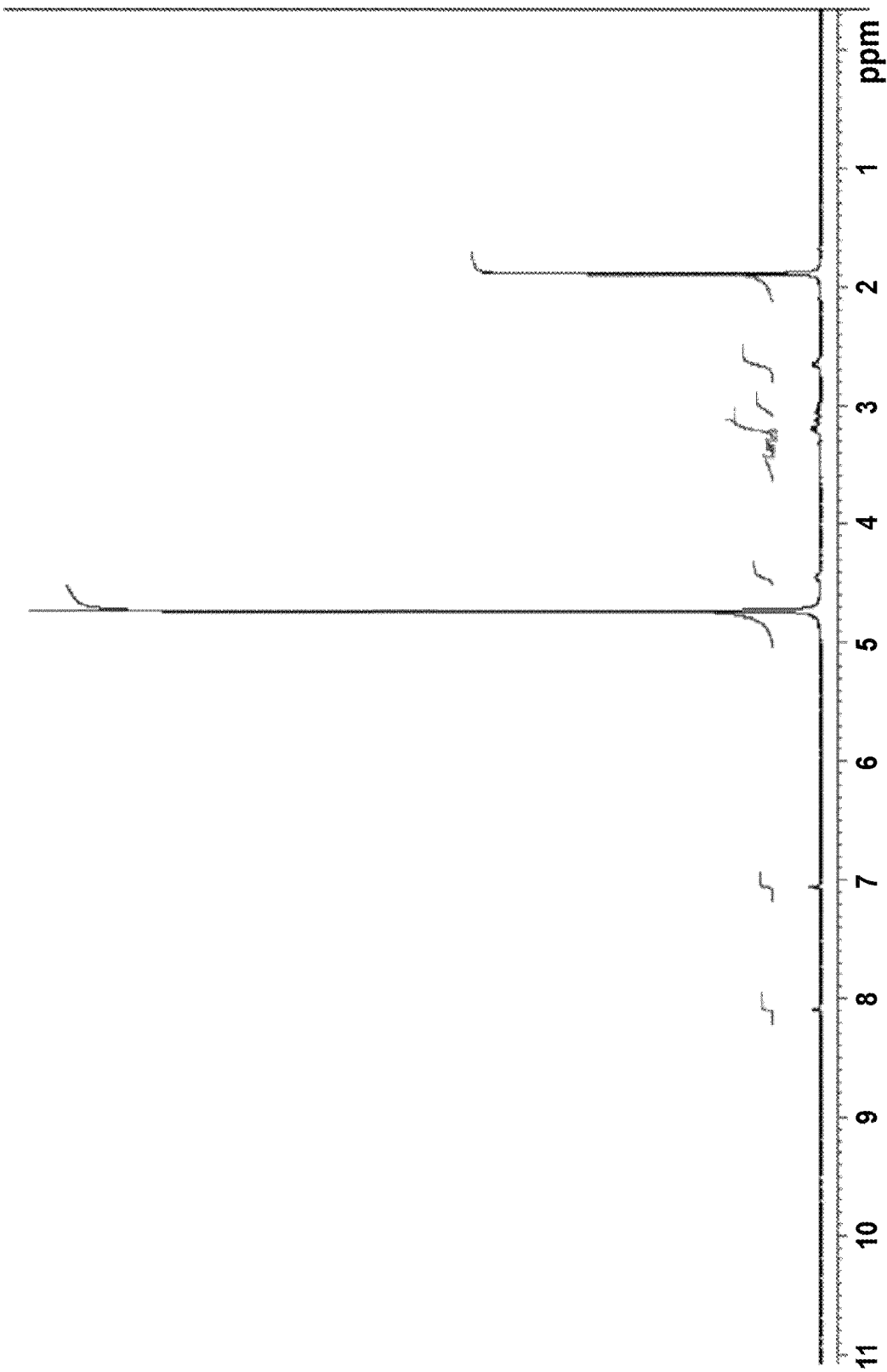

As an example, FIG. 6 shows the $D_2O$ NMR spectrum recorded on a Bruker DRX500,13400 device with an operating frequency of 500.13 MHz.

It mainly contains the residual signal of the non-deuterated solvent, and low-intensity signals corresponding to the original gamma-L-glutamylhistamine.

This indicates the absence of impurities and the insignificant dissociation of the resulting product in aqueous suspensions.

Example 3. Obtaining a Zinc Complex According to the Invention (Method No. 2)

The goal of the present method modification according to the invention is to improve the filterability of the resulting product, as well as to ensure the most uniform distribution of zinc hydroxide in the reaction mixture.

The problem of distribution uniformity is extremely important for this technique in order to be scaled, since the formation of a zinc complex with gamma-L-glutamylhistamine on the surface of zinc hydroxide prevents the reaction from proceeding further. To solve this problem, it is proposed to obtain zinc hydroxide in situ by the simultaneous addition of sodium hydroxide and zinc acetate solutions.

Synthesis "A": To a suspension heated to 70° C., 12.0 g (0.05 mol) of gamma-L-glutamylhistamine in 150 ml of water, 50 ml of 2M aqueous sodium hydroxide solution and a solution of 11.0 (0.05 mol) zinc acetate dihydrate in 80 ml of water were added drop-by-drop, simultaneously using two funnels. The reaction mixture was stirred for 4 hours at 70° C., cooled to room temperature and left overnight. The precipitate was filtered off, washed on a filter with 3×50 ml water and dried in vacuum at 45-50° C. until it reached constant weight. The yield was 21.5 g (71% of the product).

The polyamorphous complex obtained by this method was easier to separate in the form of a filtrate, compared to the complex according to Example 2, obtained in methanol using sodium methoxide.

This technique was scaled up and reproduced according to synthesis "B".

Synthesis "B": To a suspension heated to 70° C., 24.0 g (0.1 mol) of gamma-L-glutamylhistamine in 300 ml of water, 100 ml of 2M aqueous sodium hydroxide solution and a solution of 22.0 (0.1 mol) zinc acetate dihydrate in 120 ml of water were added drop-by-drop, simultaneously using two funnels. The reaction mixture was stirred for 4 hours at 70° C., cooled to room temperature and left overnight. The precipitate was filtered off, washed on a filter with 4×50 ml water and dried in vacuum at 45-50° C. until its weight remains constant, to of 44.1 g (71% of the product).

Two test runs of this method were performed and a sample for elemental analysis was obtained from each run. According to the analysis of the elemental data of these two samples, a zinc complex with gamma-L-glutamylhistamine is formed with a molar ratio of gamma-L-glutamylhistamine/zinc—1/1 as the result of the reaction (see Table 3).

TABLE 3

The results of elemental analysis of the zinc complex of gamma-L-glutamylhistamine (Method No. 2)

|  |  | C | N | H |
|---|---|---|---|---|
| Found1 | Method | 39.52 | 18.26 | 4.72 |
| Found2 | No2 «A» | 39.44 | 17.96 | 4.66 |
| Found1 | Method | 39.54 | 18.18 | 4.52 |
| Found2 | No2 «B» | 39.49 | 17.99 | 4.47 |
| Calculated |  | 39.56 | 18.45 | 4.65 |

Figure 4:
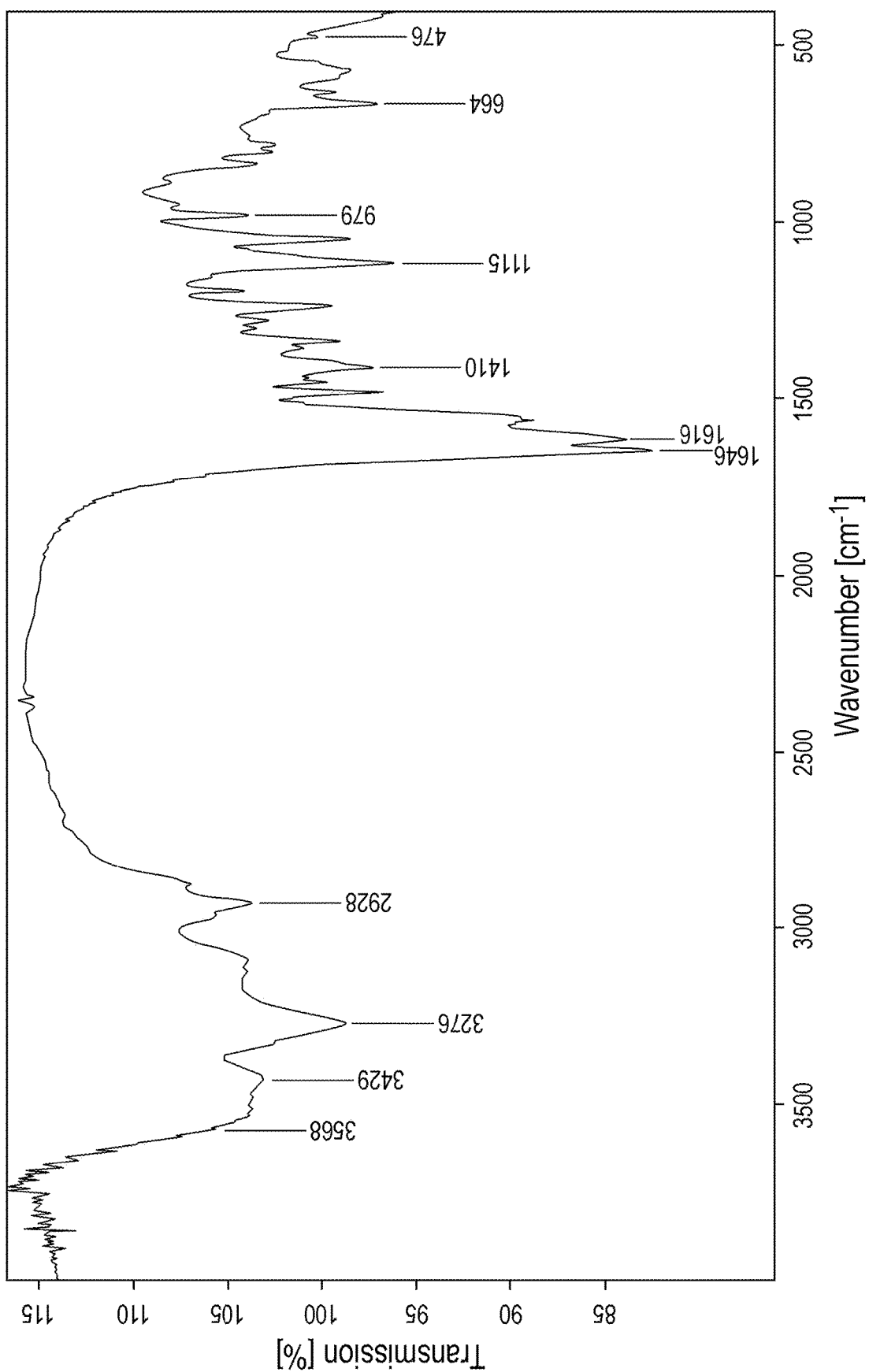
FIG. 4. IR spectrum of a sample of the zinc complex of gamma-L-glutamylhistamine related to example 3, Synthesis "A" FIG. 5. IR spectrum of a sample of the zinc complex of gamma-L-glutamylhistamine related to example 3, Synthesis "B" FIG. 6. Nuclear magnetic resonance spectrum of 1H sample containing the zinc complex of gamma-L-glutamylhistamine according to Example 2.
Figure 5:
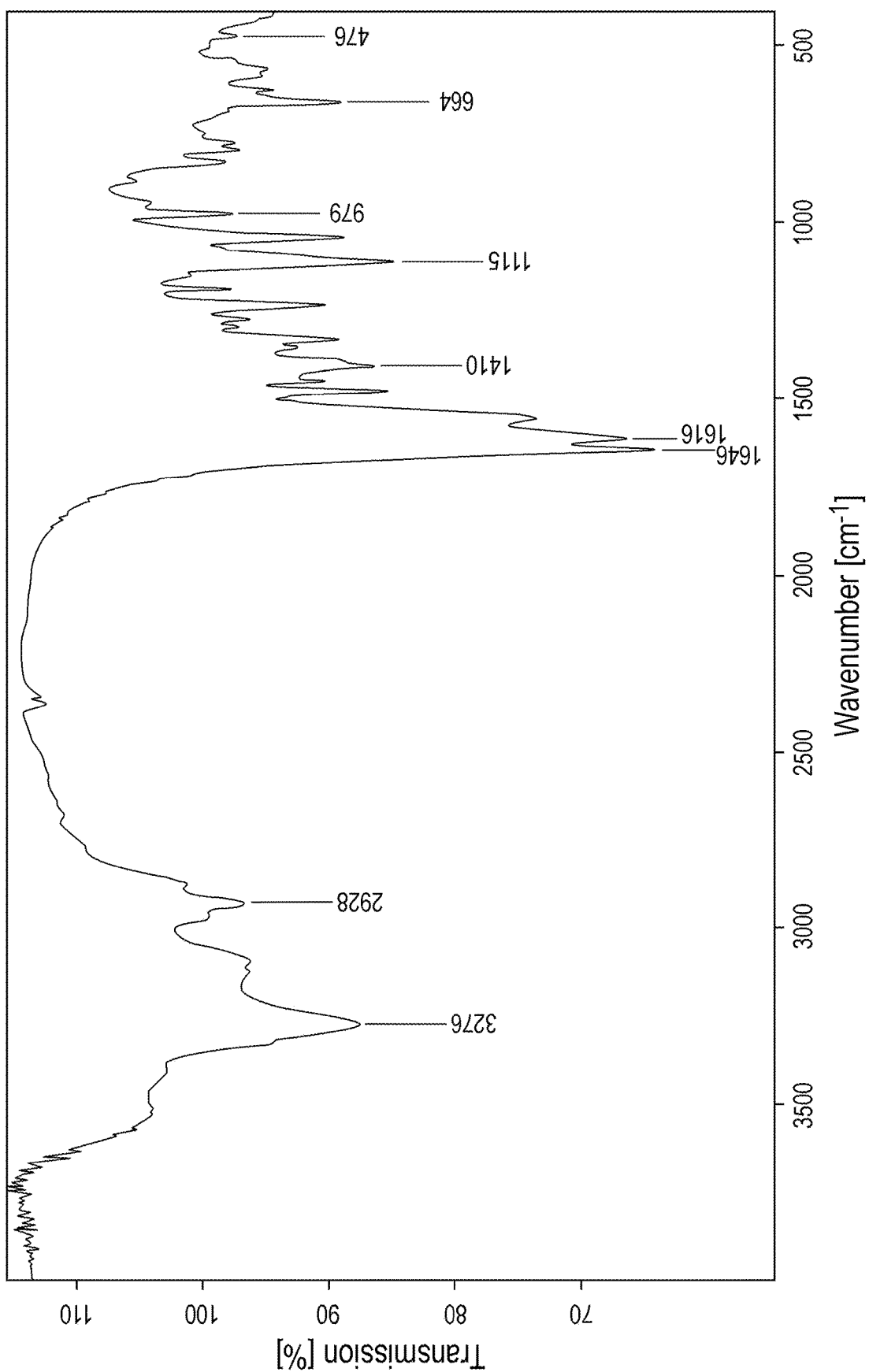

IR-spectrum of the resulting product (see FIGS. 4 and 5) is similar to the spectrum of the zinc complex of gamma-L-glutamylhistamine synthesized by Method No. 1 and these spectra do not have significant differences in the fingerprint region.

A complexometric titration of zinc was performed to confirm the complex composition and the obtained metal/ligand ratio, (see Table 4). As a result, it was shown that the zinc content in the product obtained by Method No. 2 is ~22.01, which is consistent with the theoretically calculated value (21.1%) of the corresponding zinc complex having a metal: ligand ratio of 1:1.

TABLE 4

Results of complexometric titration of the zinc complex of gamma-L-glutamylhistamine

| Method | Titration results No1 (Zn2+) | Titration results No2 (Zn2+) | Calculated |
|---|---|---|---|
| Method No1 | 21.53% | 22.03% | 21.87% |
| Method No2 «A» | 22.18% | 21.95% |  |
| Method No2 «B» | 21.55% | 22.13% |  |

Characterization of the Biological Activity of the Compound 1 Complex

The biological activity of Compound 1 of the present invention has been studied in various experiments in vitro and in vivo. In particular, the inhibitory effect of Compound 1 on the chemotaxis of immune cells was shown in experiments focused on the activity of Compound 1 in an in vivo model of atopic dermatitis. Studies of the biological activity of Compound 1 in vitro have established that Compound 1 is an inhibitor of the enzyme glutaminyl cyclase, therefore, the effect of Compound 1 on the chemotaxis of immune cells may be mediated by inhibition of the activity of glutaminyl cyclase.

Example 4. Study of the Effect of Compound 1 on the Enzymatic Activity of Human Glutaminyl Cyclase In Vitro In the studies of the effect of Compound 1 (which is the subject of the present invention) on the enzymatic activity of glutaminyl cyclase in vitro, the direct inhibitory effect of Compound 1 on recombinant intracellular human glutaminyl cyclase was discovered.

The activity of glutaminyl cyclase at various Compound 1 concentrations was studied at 25° C. using the fluorescent substrate L-glutaminyl 2-naphthylamide (Gln-bNA) [Anal Biochem. 2002 Apr. 1; 303 (1): 49-56]. The reaction mixture with a volume of 100 µl contained 50 µM of a fluorogenic substrate; ~0.2 units of human pyroglutaminyl aminopeptidase (1 unit is defined as the amount that hydrolyzes 1 micromole of pGlu-bNA per minute), and an aliquot of recombinant intracellular human glutaminyl cyclase (gQC) in 50 micromol trisaminomethane HCl and 5% glycerol, pH 8.0. The reaction was initiated by adding an aliquot of glutaminyl cyclase incubated with Compound 1 for 5 minutes to the reaction mixture.

Further progression of the reaction was monitored spectrophotometrically (excitation and emission wavelengths were 320 and 410 nm). Enzymatic activity was determined by the amount of released 2-naphthylamide (bNA), calculated based on the calibration curve. IC50 values were calculated using non-linear regression of the "inhibitor concentration"-"enzyme activity" curve.

The experiment has demonstrated that Compound 1 inhibits the activity of glutaminyl cyclase with IC50=26 µM.

Example 5. Study of the Activity of Compound 1 in a Mouse Atopic Dermatitis Model Experimental technique. The study of Compound 1 activity in the model of atopic dermatitis was carried out using the standard technique [Evidence-based Complementary and Alternative Medicine. 2012. Article ID 545497, 9 pages). For the experimental group, we selected animals of average appearance without signs of deviations, with the weight of the animal being no more than ±20% from the average value within the sex.

On days 0 and 12 of the experiment, male mice of the balb/c strain were treated with 100 µl of a 2% solution of 1-chloro-2,4-dinitrobenzene (DNCB) in ethanol applied to the previously shaved areas on the back to sensitize the body. On the 17th day, 20 µl of 2% alcohol solution of DNCB was applied to the "test" right ear of the animals twice with an interval of 1 hour. Compound 1 cream with an active substance content of 0.01 wt % was administered topically, to the "test" right ear, twice: 1 and 13 hours after the last application of DNCB to the ear. The following were used as a comparison/reference/control medications: Methylprednisolone aceponate (0.13 ointment for external use), pyrithione zinc (0.2% cream for external use), pimecrolimus (1% cream for external use) and cream for external use containing gamma-L-glutamylhistamine 0.01%. On the 18th day, the animals were euthanized and the histological analysis of the affected ear was performed. Histological sections with a thickness of 5 µm were stained with hematoxylin-eosin.

Evaluation of microscopic changes demonstrating dermatitis was carried out according to the following scale:
1) Acanthosis—thickening of the epidermis and epithelium with lengthening of the interpapillary processes:
0 points—no pathology;
0.5 points—pathology detected, but very weakly expressed;
1 point—moderate to severe pathology;
2 points—severe pathology.
2) Hyperkeratosis is a non-inflammatory characteristic of skin condition characterized by a significant thickening of the stratum corneum or a delay in its normal rejection:
0 points—no pathology;
0.5 points—pathology detected, but very weakly expressed;
1 point—the clear presence of the indicated pathology.
3) Pustules (abscesses)—cavitary acute inflammatory elements with purulent contents:
0.5 points—single manifestations of pathology;
1 point—mild pathology;
2 points—moderate to severe pathology;
3 points—severe pathology;
4 points—total pathology.
4) Cyst is a structure of a rounded or oval shape, that is lined by stratified squamous keratinizing epithelium and filled with layers of horny masses, which develops when hyperplasia of the epithelium (acanthosis) is present:
0 points—no pathology;
0.5 points—pathology detected, but very weakly expressed;
1 point—the clear presence of the indicated pathology.
5) Inflammation:
0 points—no pathology;
0.5 points—single manifestations of pathology;
1 point—mild pathology;
2 points—moderate to severe pathology;
3 points—severe pathology;
4 points—total pathology.
6) Edema:
0 points—no pathology;
0.5 points—single manifestations of pathology;
1 point—mild pathology;
2 points—moderate to severe pathology;
3 points—severe pathology;
4 points—total pathology.

The data obtained were verified using the Grubbs test, also known as the maximum normalized residual test a test used to detect outliers in a data set. The values identified as "outliers" in this test were not used for further analysis. Descriptive statistics were used for all data: the mean (M) and standard error of the mean (m) were calculated. The normal distribution of the values obtained in the experiment was verified using the Kolmogorov-Smirnov test. In the case of a normal distribution, Student's t-test was used to assess intergroup differences. In the case of a non-normal distribution, the Kruskal-Wallis test (with Dunn's post-analysis) was used to compare several groups. Statistical analysis was performed using the GraphPad Prism software. 5.0. Differences were determined at a 5% confidence level.

Figure 7:
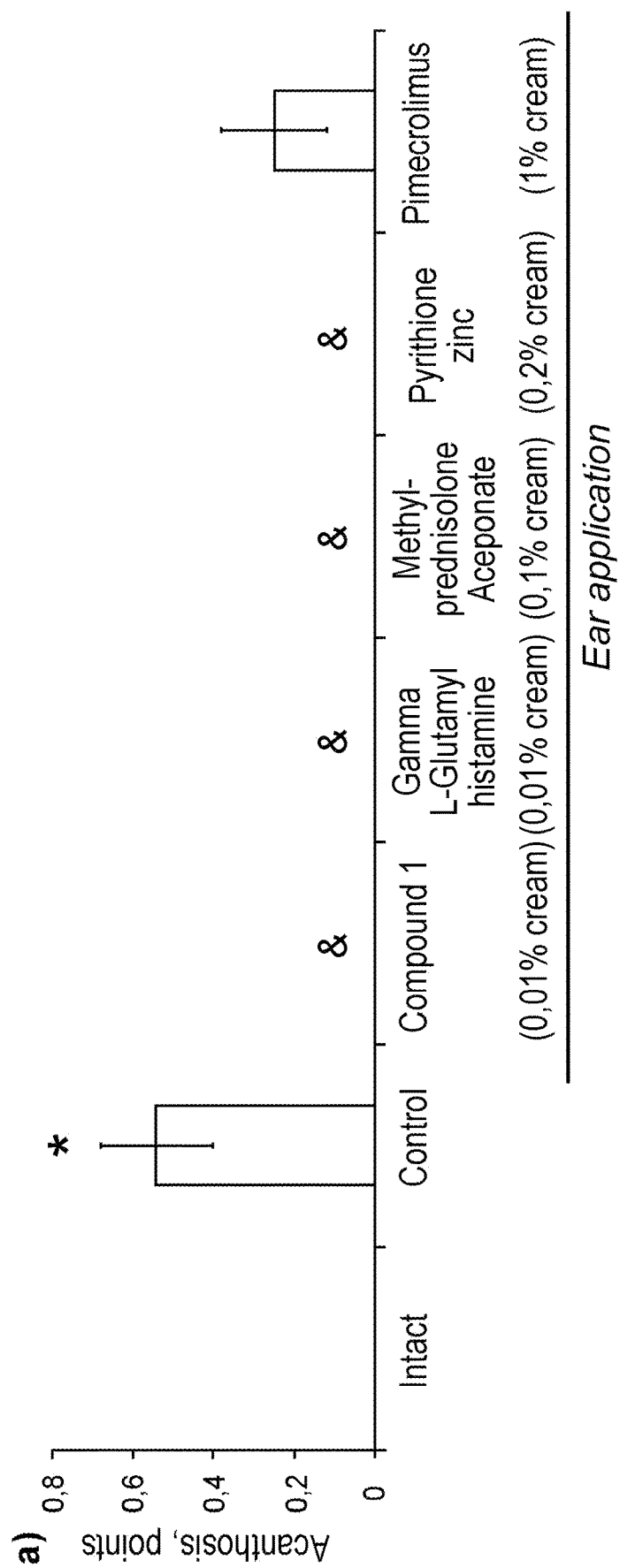
FIG. 7. Pharmacological action of a cream containing Compound 1 (0.01,) applied on skin lesions in a mouse model of atopic dermatitis according to histological analysis data.
Figure 7:
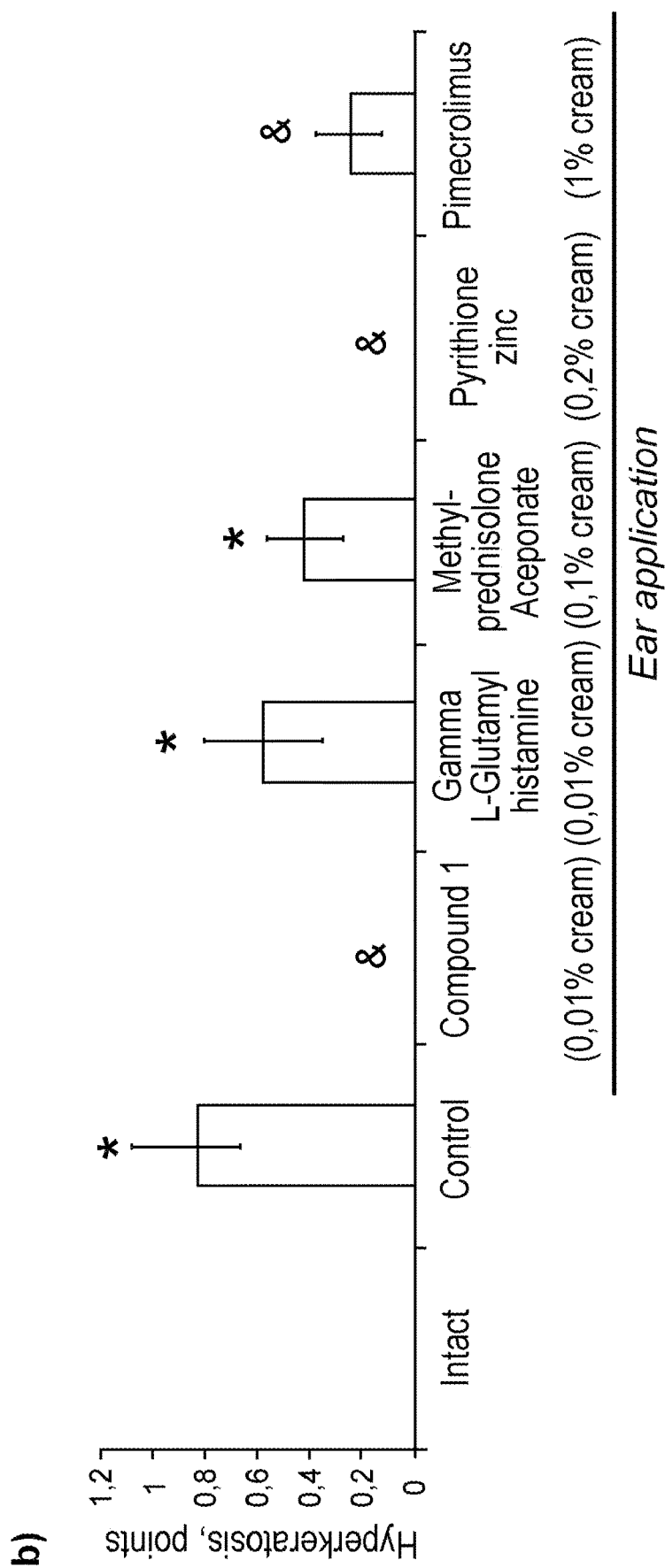
Figure 7:
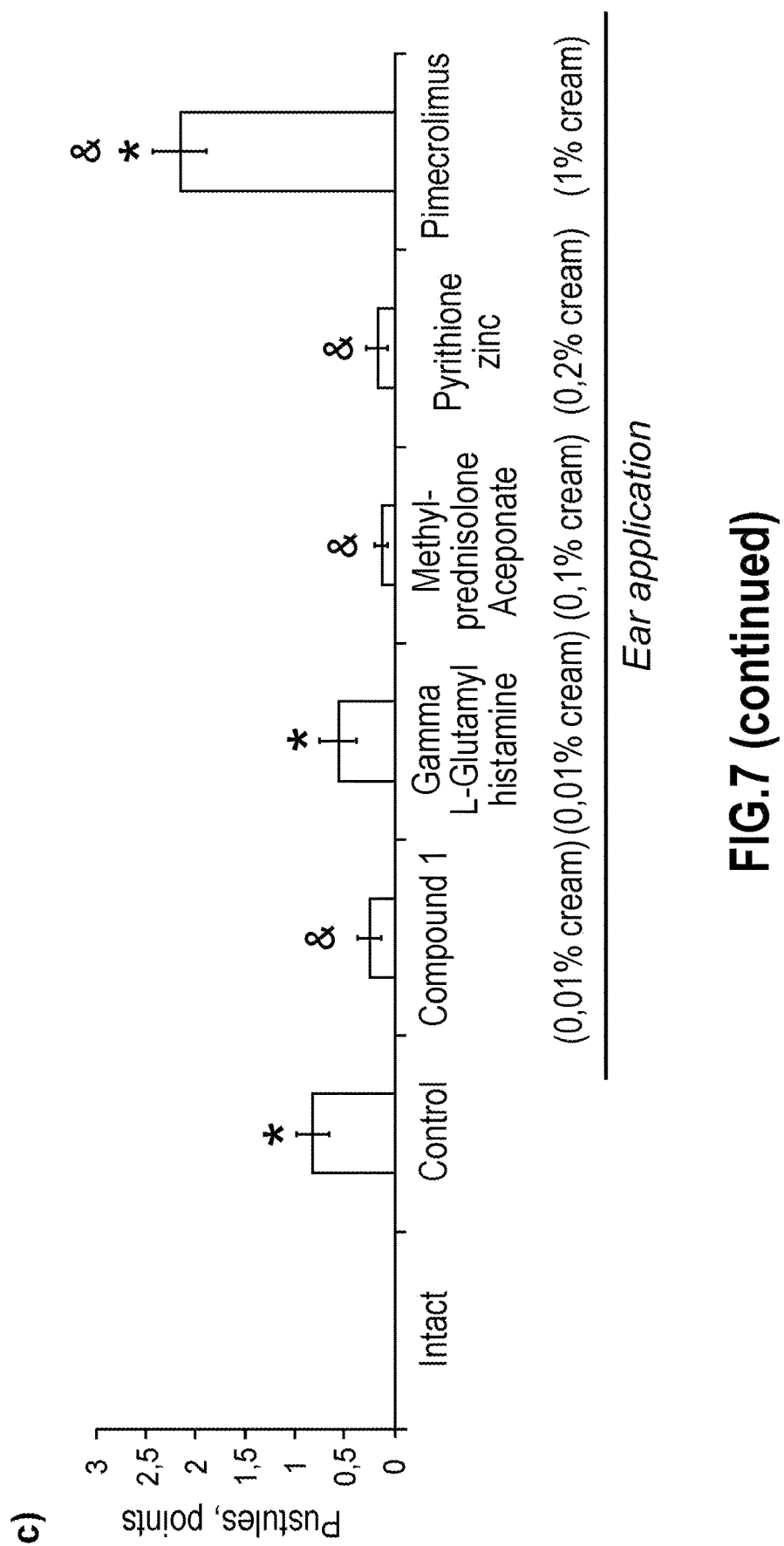
Figure 7:
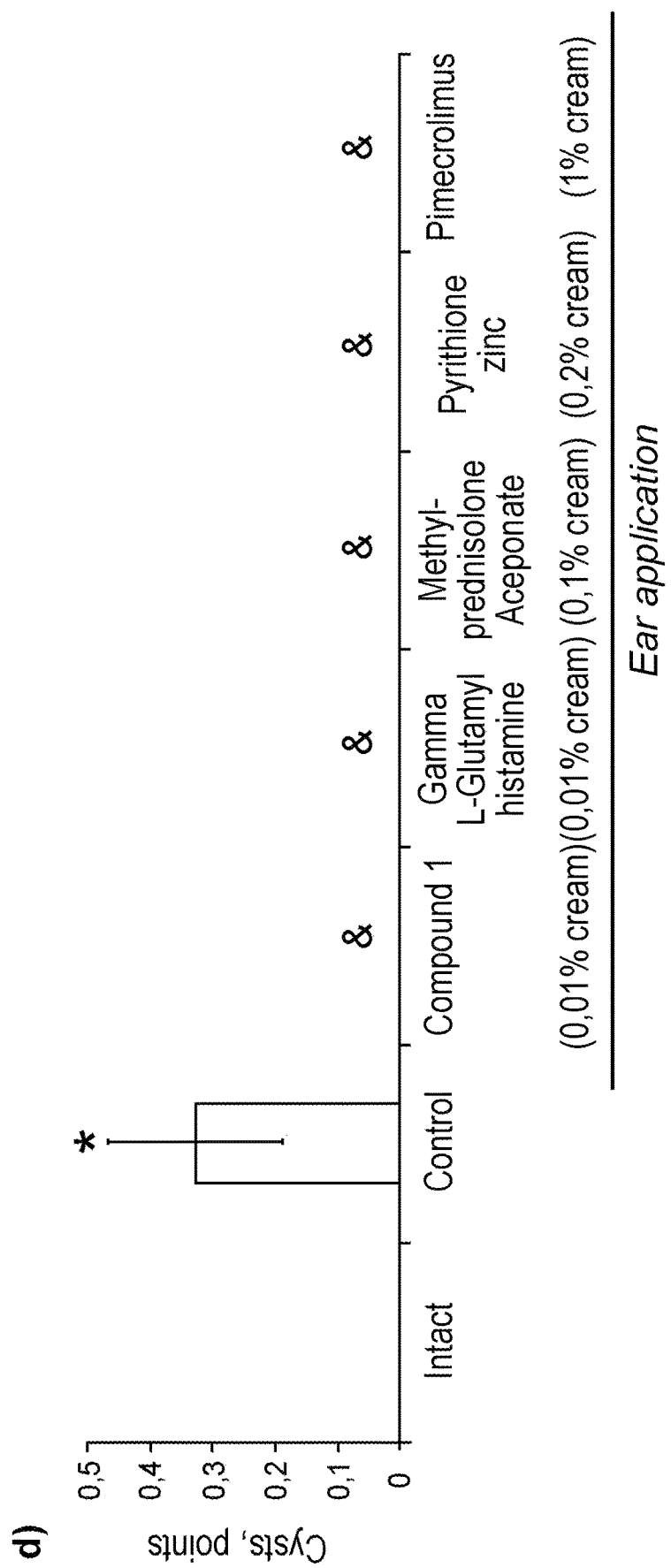
Figure 7:
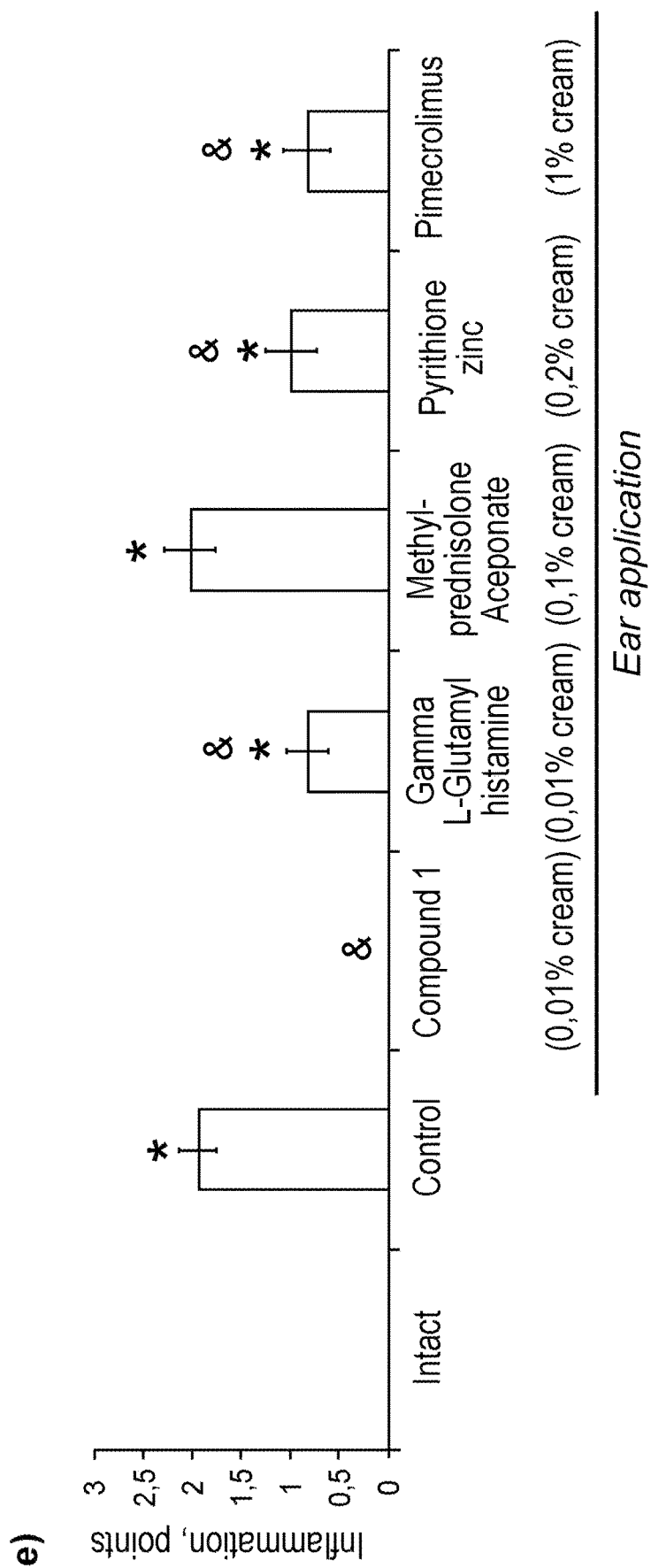
Figure 7:
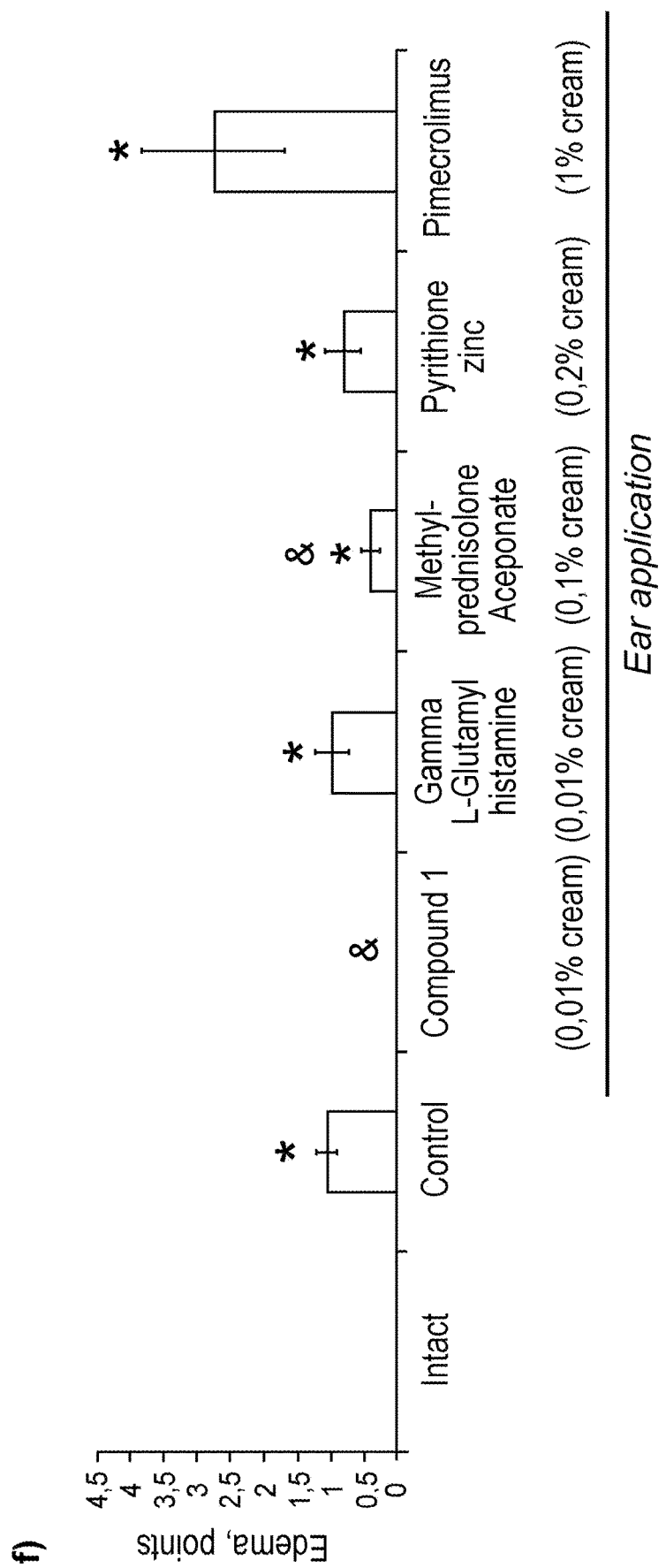
Figure 8:
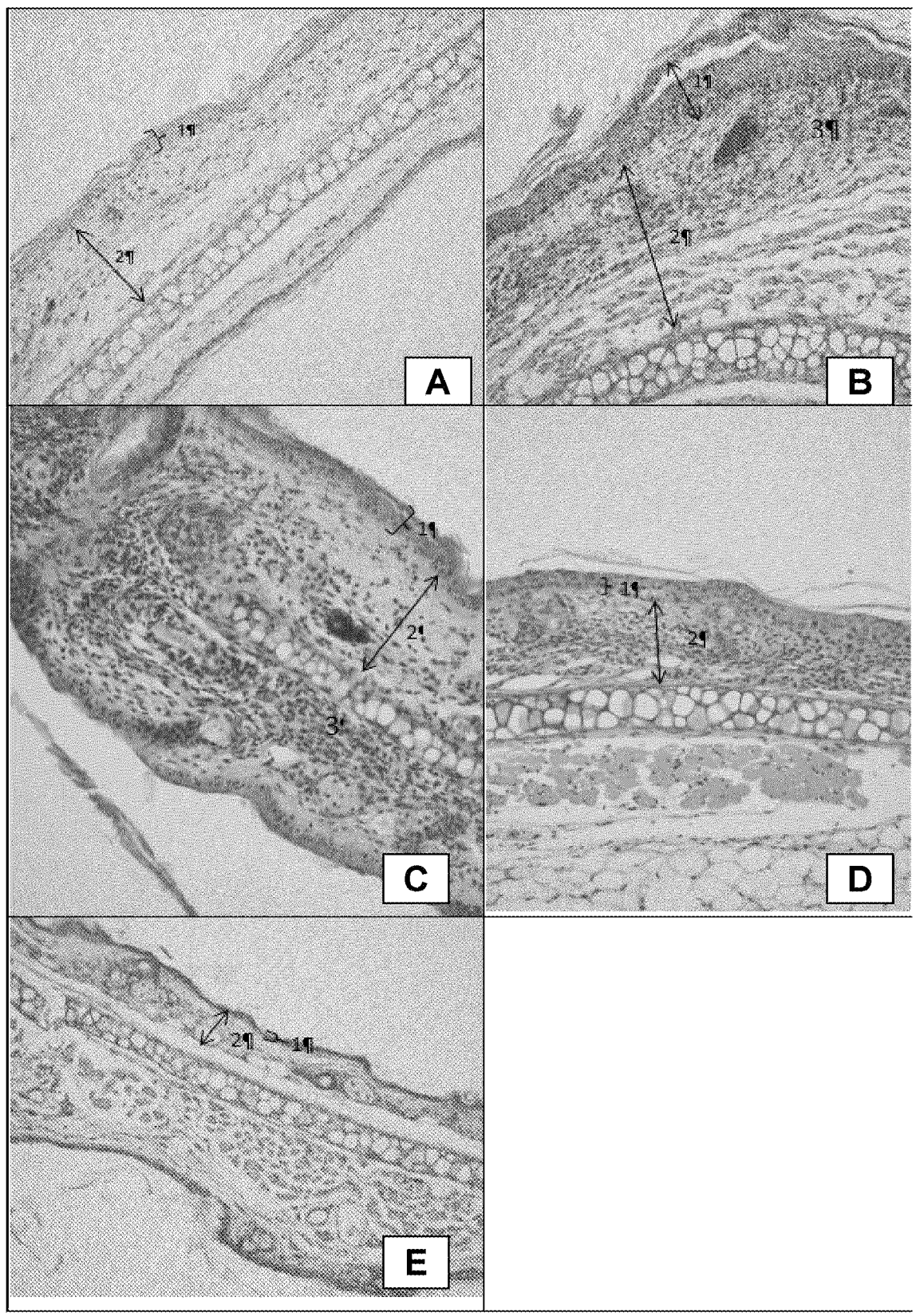
FIG. 8. Histological sections of the skin of the affected mice ear (animal model of atopic dermatitis).

The results of the experiments are shown on FIGS. 7 and 8. As can be seen from the data shown in FIG. 7, the pharmacological effect of a cream containing Compound 1 (0.01 wt}) on skin lesions in mouse atopic dermatitis model according to histological analysis was evaluated by the following: a) acanthosis (points), b) hyperkeratosis (points), c) pustules (points), d) cysts (points), e) inflammation (points), f) edema (points). Experiments were carried out in accordance with: Evidence-based Complementary and Alternative Medicine. 2012. Article ID 545497, 9 pages. Note: *—significance of the difference ($P<0.05$) with the intact group, &—significance of the difference ($P<0.05$) with the control.

FIG. 8 shows histological sections of the skin of the affected ear in a mouse atopic dermatitis model, stained with hematoxylin-eosin, with a magnification of ×20.

A—Group of intact animals; B—Pathology control; C—Advantan (Methylprednisolone aceponate, ointment 0.1%); D—Pimecrolimus (Elidel 1% cream); E—Compound I Cream 0.01%. 1—epidermis; 2—dermis; 3—inflammatory infiltrate. Experiments were carried out in accordance with: Evidence-based Complementary and Alternative Medicine. 2012. Article ID 545497, 9 pages.

The application of Compound 1 (0.01 wt % cream) to the skin reduced the influx of inflammatory cells (monocytes, dendritic cells, eosinophils and neutrophils) into the epidermis and dermis of the skin to the level of intact animals, as well as other microscopic manifestations of atopic dermatitis. It is important to note that, in terms of the action, Compound 1 (zinc complex of gamma-L-glutamylhistamine) shows significant improvement in comparison with the action of the gamma-L-glutamylhistamine ligand. Thus, the therapeutic activity of Compound 1 cannot be explained by the activity of gamma-L-glutamylhistamine alone. In terms of the effectiveness, the Compound 1 cream showed superior performance in comparison with the reference drugs: methylprednisolone aceponate, zinc pyrithione and pimecrolimus. The results obtained allow us to conclude that Compound 1 has demonstrated an improved therapeutic effect in treating atopic dermatitis.

CONCLUSIONS

Thus, the studies carried out showed that Compound 1 is effective in inhibiting the glutaminyl cyclase enzyme. In a model of atopic dermatitis, Compound 1 has been shown to inhibit the influx of inflammatory cells (monocytes, dendritic cells, eosinophils and neutrophils) in vivo, as well as other microscopic manifestations of atopic dermatitis.

Although the invention has been described with reference to the disclosed embodiments, it should be apparent to those skilled in the art that the specific experiments described in detail are provided only for the purpose of illustrating the present invention and should not be construed as limiting the scope of the invention in any way. It should be understood that various modifications may be possible without departing from the essence of the present invention.

The invention claimed is:

1. A method of preparing a zinc complex with gamma-L-glutamylhistamine, comprising:
   stirring a mixture of zinc acetate and gamma-L-glutamylhistamine in a polar solvent;
   precipitating the product; and
   drying the resulting product, which is a zinc complex with gamma-L-glutamylhistamine with a metal:ligand ratio of 1:1.

2. The method of claim 1, wherein the solvent is methanol or water, or a combination thereof.

3. The method of claim 1, wherein aqueous zinc acetate is used.

4. The method of claim 2, wherein the stirring of the mixture is carried out at a temperature of 15 to 50 degrees Celsius and the solvent is methanol.

5. A zinc complex with gamma-L-glutamylhistamine, wherein the molar ratio of metal/ligand is 1/1.

6. The zinc complex with gamma-L-glutamylhistamine of claim 5, which is prepared by stirring an equimolar mixture of zinc acetate and gamma-L-glutamylhistamine in a solvent, followed by isolation of the complex as a product.

7. The zinc complex with gamma-L-glutamylhistamine of claim 5, wherein the IR spectrum of the solid sample of the complex demonstrates bands at 1616 $cm^{-1}$, 1646 $cm^{-1}$, and 3276 $cm^{-1}$.

8. A method of treating atopic dermatitis in a subject in need thereof, comprising administering to the subject an effective amount of the zinc complex of claim 5.

9. The method of claim 3, wherein the aqueous zinc acetate is zinc acetate dihydrate.

10. The method of claim 4, wherein the stirring of the mixture is carried out at a temperature of 15 to 40 degrees Celsius.

11. The method of claim 2, wherein the stirring of the mixture is carried out at a temperature of 15 to 90 degrees Celsius when the solvent is water.

12. A method of treating atopic dermatitis in a subject in need thereof, comprising administering to the subject an effective amount of the zinc complex of claim 7.

13. A zinc complex with gamma-L-glutamylhistamine, characterized by the following results of elemental analysis of the zinc complex of gamma-L-glutamylhistamine:
   (i) Found 1: C: 39.17; H: 4.73; N: 18.02;
      Found 2: C: 37.26; H: 4.80; N: 18.110;
      Calculated: C: 39.56; H: 4.65; N: 18.45;
   or
   (ii) Found1: C: 39.52; N: 18.26; H: 4.72;
      Found2: C: 39.44; N: 17.96; H: 4.66;
      Found1: C: 39.54; N: 18.18; H: 4.52;
      Found2: C: 39.49; N: 17.99; H: 4.47;
      Calculated: C: 39.56; N: 18.45; H: 4.65.

14. A zinc complex with gamma-L-glutamylhistamine, characterized with the following results of complexometric titration of the zinc complex of gamma-L-glutamylhistamine:
   Titration results No. 1 ($Zn^{2+}$): 21.53%, 22.18%, 21.55%;
   Titration results No. 2 ($Zn^{2+}$): 22.03%, 21.95%, 22.13%;
   Calculated: 21.87%.

* * * * *